(12) United States Patent
Focke et al.

(10) Patent No.: US 7,244,431 B2
(45) Date of Patent: Jul. 17, 2007

(54) ALLERGY VACCINES AND THEIR PREPARATION

(76) Inventors: Margarete Focke, Utendorfgasse 22, A-1140, Wein (AT); Vera Mahler, Wilhelmstrasse 4, D-91054, Erlangen (DE); Wolfgang R. Sperr, Iglaseegasse 9, A-1190, Wein (AT); Peter Valent, Schulgasse 7/18, A-1170, Wein (AT); Dietrich Kraft, Rebenweg 1/18/1, A-1170 Wien (AT); Rudolf Valenta, Beethovenstrasse 18, A-2604, Theresienfeld (AT)

( * ) Notice: Subject to any disclaimer, the term of this patent is extended or adjusted under 35 U.S.C. 154(b) by 117 days.

(21) Appl. No.: 10/026,911

(22) Filed: Dec. 27, 2001

(65) Prior Publication Data

US 2003/0078201 A1    Apr. 24, 2003

(30) Foreign Application Priority Data

Dec. 28, 2000    (EP) .................................. 00128659

(51) Int. Cl.
*A61K 39/00*    (2006.01)
(52) U.S. Cl. .......................... 424/185.1; 514/2; 514/8; 530/324; 530/868; 424/810
(58) Field of Classification Search ................. 514/12; 424/185.1, 275.1
See application file for complete search history.

(56) References Cited

U.S. PATENT DOCUMENTS 6,878,376 B2*    4/2005    Spertini ................... 424/185.1

FOREIGN PATENT DOCUMENTS

| EP | 0 714 662 | 7/1994 |
|---|---|---|
| WO | WO 96/27005 | 3/1996 |
| WO | WO 97/05258 | 8/1996 |
| WO | WO 97/24139 | 9/1996 |

OTHER PUBLICATIONS

Friedl-Hajek et al., Clinical and experimental Allergy, 1999, vol. 29, pp. 478-487.*
Ferreira et a., FASEB Journal, vol. 12, pp. 231-242, 1998.*
Friedl-Hajek et al., Molecular Immunology, 1999, 36:639-645.*
Swoboda et al. J. Biol. Chem. 1995, 270:2607-2613.*
Colman, P.M., Research in Immunology, 1994, 145:33-36.*
Vik et al., Int Arch Allergy Immunol, 1993, 101:89-94.*
Mandler et al., J. Immunol. 1993, 150:407-418.*
Harlow et al., Antibodies, A Laboratory Manual, 1988, Cold Spring Harbor Laboratory, pp. 72-87.*
Blumenthal et al. in Allergens and Allergen Immunotherapy, 3rd edition, 2004, pp. 37-50.*
Denépoux, S. et al., "Molecular characterization of human IgG monoclonal antibodies specific for the major birch pollen allergen Bet v 1. Anti-allergen IgG can enhance the anaphylactic reaction," *FEBS Letters*, 465: 39-46 (2000).
Gajhede, M. et al., "X-ray and NMR structure of Betv1, the origin of birch pollen allergy," *Nature Structural Biology*, 3(12): 1040-45 (Dec. 1996).
Niederberger, V. et al., "IgE antibodies to recombinant pollen allerens (Phl p 1, Phl p 2, Phl p 5, and Bet v 2) account for a high percentage of grass pollen-specific IgE," *J. Allergy Clin. Immunol.*, 101: 258-264 (Feb. 1998).
Valent, P. et al., "Interleukin 3 activates human blood basophils via high-affinity binding sites," *Proc. Natl. Acad. Sci. USA*, 86: 5542-46 (Jul. 1989).
Vrtala, S. et al., "Conversion of the Major Birch Pollen Allergen, Bet v 1, into Two Nonanaphylactic T Cell Epitope-containing Fragments," J. Clin, Invest., 99(7): 1673-81 (Apr. 1997).
Vrtala, S. et al., "Properties of Tree and Grass Pollen Allergens: Reinvestigation of the Linkage between Solubility and Allergenicity," *Int. Arch. Allergy Immunol.* 102; 160-69 (1993).
European Search Report, EP 00 12 8659.
M. Focke et al.; "Nonallergenic Peptides from Surface-Exposed Areas or B-Cell Epitopes of Allergens for Specific Immunotherapy", *Int. Arch Allergy Immunol*, 124: 398-399 (2001).
E. Ganglberger et al.; "IgE Mimotopes of Birch Pollen Allergen Bet v. 1 Induce Blocking IgG in Mice", *Int. Arch Allergy Immunol*, 124: 395-397 (2001).
R. Furmonaviciene et al.; "The Use of Phage-Peptide Libraries to Define the Epitope Specificity of a Mouse Monoclonal Anti-Der p 1 Antibody Representative of a Major Component of the Human Immunoglobulin E Anti-Der p 1 Response", *Clinical and Experimental Allergy*, 29: 1563-1571 (1991).
E. Ganglberger et al.; "Allergen Mimotopes for 3-Dimensional Epitope Search and Induction of Antibodies Inhibiting Human IgE", *FASEB Journal*, 14: 2177-2184 (2000).

* cited by examiner

*Primary Examiner*—G. R. Ewoldt
*Assistant Examiner*—Michael Szperka
(74) *Attorney, Agent, or Firm*—Reed Smith, LLP

(57) ABSTRACT

The present invention relates to a pharmaceutical composition containing a peptide and a pharmaceutically acceptable carrier or diluent wherein the peptide has a length of 8 to 50 amino acids, at least three preferably consecutive amino acids of the peptide are identical to at least three amino acids which appear in close vicinity on the molecular surface of an allergenic protein, and said at least three amino acids are solvent-exposed amino acids in the allergenic protein. The invention also concerns a method for the preparation of the pharmaceutical composition.

1 Claim, 3 Drawing Sheets

ALLERGY VACCINES AND THEIR PREPARATION

Figure 1:
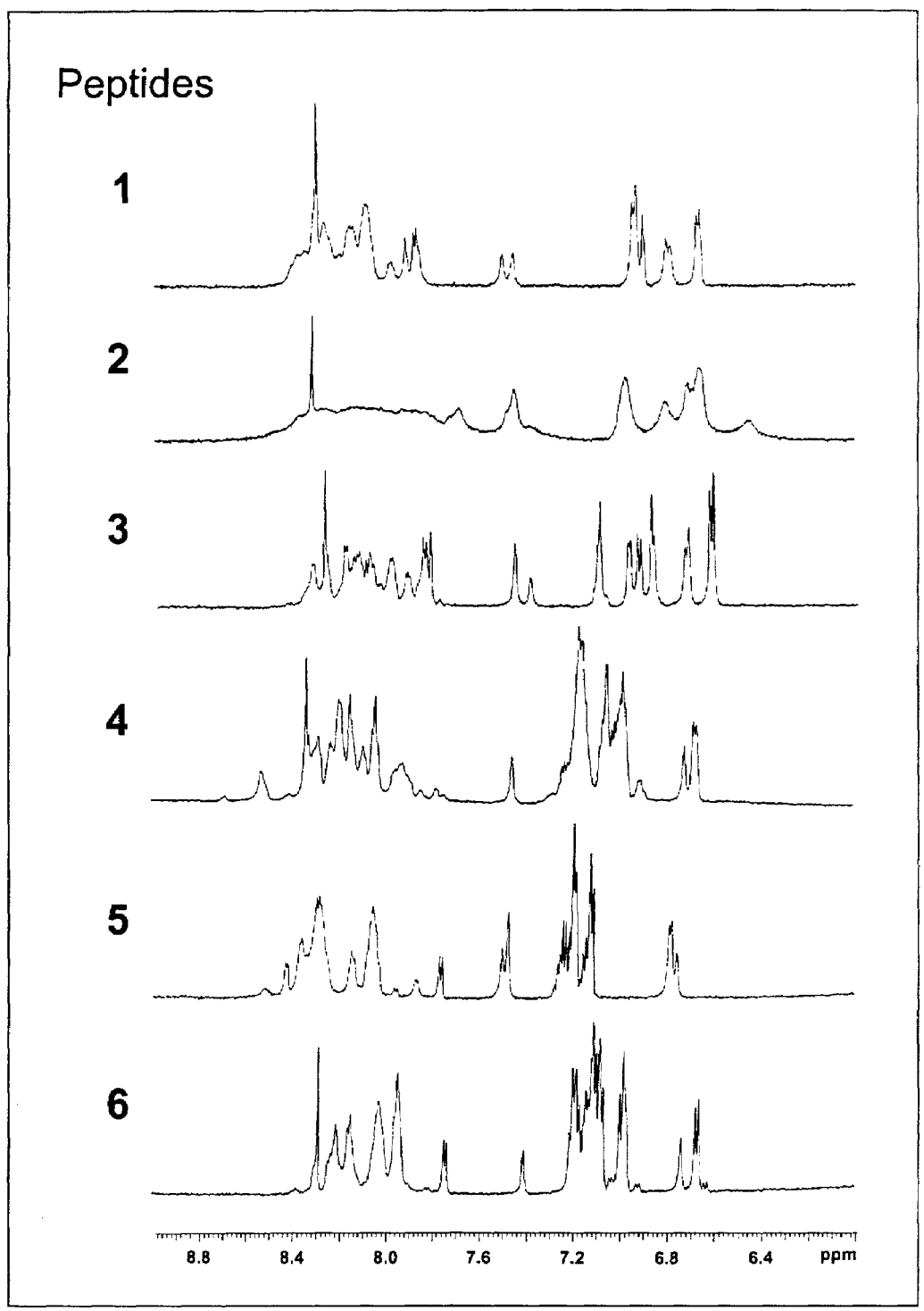

Almost 500 million individuals suffer from Type I allergy, a genetically determined hypersensitivity disease which is based on the formation of IgE antibodies against per se harmless antigens (i.e., allergens). In sensitized patients, allergen contact can induce a variety of symptoms ranging from allergic rhinoconjunctivitis, atopic dermatitis, diarrhea, bronchial asthma, and sometimes life-threatening anaphylaxis. The immediate symptoms of allergic disease are caused by crosslinking of effector cell-bound IgE antibodies by allergens which triggers the release of biologically active mediators (e.g., histamine, leukotrienes). In addition, allergen presentation to T cells may be also mediated by IgE antibodies and induce chronic symptoms of allergic disease (e.g., atopic dermatitis, chronic asthma) via T cell activation and release of proinflammatory cytokines.

The only curative approach towards allergy treatment, allergen-specific immunotherapy, is based on the continuous administration of the disease-eliciting allergens to the patients in order to induce allergen-specific non-responsiveness. Multiple studies document the clinical efficacy of specific immunotherapy, but two major disadvantages must be overcome: First, systemic administration of allergens can induce life-threatening anaphylactic side effects. Second, immunotherapy is performed with allergen extracts consisting of difficult to standardize mixtures of allergenic and non-allergenic components which cannot be tailored to the individual patients' specific sensitization profile.

It is an object of the invention to provide an advantageous pharmaceutical composition for the treatment of allergic disorders.

Surprisingly, it has been found that the administration of peptides comprising solvent-exposed amino acids of an allergen lead to the production of protective antibodies.

Therefore, the present invention relates to a method for the preparation of a pharmaceutical composition which comprises as a first step the determination which amino acids of a given allergenic protein are solvent-exposed on the surface of the allergenic protein. As a second step the method comprises the preparation of a peptide having a length of 8 to 50 amino acids wherein at least three preferably consecutive amino acids of the peptide are identical to at least three amino acids which appear in close vicinity on the molecular surface of the allergenic protein with at least three amino acids being solvent-exposed amino acids of the allergenic protein. The peptide may then be admixed with a pharmaceutically acceptable carrier (e.g., KLH) or diluent, e.g. with a buffer and/or salt solutions. Preferably, said at least three amino acids appear on the molecular surface of the allergenic protein within a surface patch of approximately 500 square Angstrom.

More preferably, the present invention relates to a method for the preparation of a pharmaceutical composition which comprises as a first step the determination which amino acids of a given allergenic protein are solvent-exposed on the surface of the allergenic protein. As a second step the method comprises the preparation of a peptide having a length of 8 to 50 amino acids wherein at least five consecutive amino acids of the peptide are identical to at least five consecutive amino acids of the amino acid sequence of the allergenic protein with the at least five consecutive amino acids being solvent-exposed amino acids of the allergenic protein. The peptide may then be admixed with a pharmaceutically acceptable carrier or diluent, e.g. with a buffer and/or salt solution.

In another preferred embodiment the method comprises as a further step the addition of an adjuvant. Adjuvants that are known in the art and may be used according to the invention are e.g. $Al(OH)_3$.

The peptide may be prepared by synthetic methods known in the art such as solid phase synthesis. The peptide may also be prepared by expression of recombinant DNA. A cDNA sequence encoding the peptide may be introduced into a host such as *E. coli* cells and expressed. Following expression, the peptides are recovered by known purification methods. The method of recombinant production of peptides may be preferred when longer peptides are used for the preparation of the pharmaceutical composition. The method of synthetically preparing the peptides is preferred when shorter peptides are employed.

In the first step of the method of the invention, it is determined which amino acids of a given allergenic protein are solvent-exposed on the surface of the allergenic protein. Any known allergenic protein may be used for the design of the peptides. An allergen source may be selected against which a high percentage of allergic patients is sensitized. Preferred allergenic proteins are derived from plants. A preferred allergen source is the birch pollen, because it is widely distributed in Europe, North America and Australia. Almost 25% of allergic patients suffer from allergy to the major birch pollen allergen Bet v 1. Bet v 1 contains most of the IgE epitopes present in pollens of trees belonging to the Fagales order (birch, alder, hazel, oak, hornbeam) and in plant-derived fruit. The cDNA and amino acid sequence as well as the three-dimensional structure of Bet v 1 have been determined and recombinant Bet v 1 which equals the natural Bet v 1 wild type has been produced by recombinant DNA technology. Further allergenic proteins that can be envisaged are e.g. the major grass pollen (e.g. group 1, group 2, group 5 etc.) mite (e.g., Der p 2), bee venom (e.g., phospholipase) and animal hair dander allergens (e.g., Cat: Fel d 1).

In one embodiment the solvent-exposed amino acids are determined by examination of the three-dimensional structure of the allergenic protein. Amino acids which are on the surface of the protein and not buried in the protein are considered as being solvent-exposed. Within the meaning of this application an amino acid is solvent exposed if it has a relative solvent accessibility of at least 16%, preferably at least 25%. Solvent accessibility can be determined according to residue hydrophobicity as described in Rost and Sander (1994) Proteins 20, 216-226. The three-dimensional structure of the protein may be determined by X-ray crystallography or NMR.

If the amino acid sequence of the protein is known, it is also possible to perform a hydrophilicity analysis to determine which amino acids within the sequence have a high hydrophilicity index and thus a high probability of being exposed on the surface. Another possibility is to perform a "surface probability analysis" to find out which amino acids have the highest probability to be exposed to the solvent.

If neither the sequence nor the three-dimensional structure of the allergenic protein is known, it is usually necessary to clone the gene encoding the allergenic protein. This can be done by methods known in the art.

In some cases IgE epitopes have been determined for an allergen. Such epitopes may also be used for the design of peptides, since these epitopes are on the surface of the allergenic protein.

Once it is known which amino acids within the amino acid sequence of the allergenic protein are solvent-exposed, a peptide is prepared comprising at least five consecutive amino acids which are identical to at least five consecutive solvent-exposed amino acids of the allergenic protein. The peptide has a length of 8 to 50 amino acids. Preferably, the minimum length of the peptide is twelve, more preferably 15, still more preferably 18, most preferably 21 amino acids. The maximum length of a peptide preferably is 45, more preferably 40, most preferably 35 amino acids. The most preferred length of the peptide is within a range of 21 to 35 amino acids.

It is also preferred that at least eight consecutive amino acids of the peptide are identical to at least eight consecutive solvent-exposed amino acids of the allergenic protein. Most preferably at least ten consecutive amino acids of the peptide are identical to at least 10 consecutive solvent-exposed amino acids of the allergenic protein.

The peptides used for the preparation of the pharmaceutical composition may also comprise amino acids which are not derived from the allergenic protein. N-terminal or C-terminal to the at least five consecutive solvent-exposed amino acids, amino acids derived from another source or artificially designed amino acids may be added. It is preferred, however, that almost the complete sequence of the peptide is derived from the allergenic protein. In a particular embodiment, only one amino acid within the peptide sequence is not derived from the amino acid sequence of the allergenic protein. Preferably, this is the N-terminal or the C-terminal amino acid of the peptide. Most preferably, this amino acid is a cysteine residue which allows coupling of the peptide to various carrier molecules such as keyhole limpet hemocyanin (KLH).

In a further embodiment the peptide comprises at least the N-terminal or C-terminal five amino acids of the allergenic protein. The N- and C-termini often are solvent-exposed.

In another embodiment the complete peptide sequence is derived from the amino acid sequence of the allergenic protein.

Preferably, the peptides prepared according to the invention upon administration lead to the production of IgG antibodies which react with the protein from which the peptides are derived. More preferably, these IgG antibodies are "blocking antibodies" or "protective antibodies" which prevent IgE antibodies from binding to the respective allergenic protein from which the peptides are derived. A significant reduction of allergic symptoms may be achieved in this way.

Another preferred feature of the peptides is that they do not elicit an IgE response against themselves upon administration, i.e. they are hypoallergenic or non-allergenic.

The amount of the peptide administered can be 0.1 µg to 500 µg. The amount may vary depending on the mode of treatment. During immunotherapy treatment about 50 µg can be adminsistered in a volume of 100 µl per injection. In a particular embodiment, more than one peptide is contained in the pharmaceutical composition. It is preferred that two, three, four, five or six different peptides are contained. These different peptides may be derived from the same allergen, it is also possible, however, that they are derived from different proteins. Thus, by administration of a single pharmaceutical composition an antiallergic effect with respect to different allergens can be achieved.

Another aspect of the present invention is a pharmaceutical composition prepared by a method described supra. The pharmaceutical composition contains a peptide having a length of 8 to 50 amino acids characterized in that at least five consecutive amino acids of the peptide are identical to at least five consecutive solvent-exposed amino acids of an allergenic protein. The preferred properties and characteristics of the peptide contained in the pharmaceutical composition of the invention have been described for the method for its preparation.

The pharmaceutical composition preferably is a vaccine composition. It may be administered to allergic patients via various routes. Preferably, the pharmaceutical composition is administered by subcutaneous injection. Other modes of administration are intramuscular or intravenous injection. Other preferred modes are sublingual, oral or nasal administration.

The systemic administration of allergens to allergic patients in the course of specific immunotherapy as practiced in the art harbors the risk of inducing life-threatening anaphylactic reactions. Furthermore, allergen extracts currently used for treatment contain a variety of allergenic and non-allergenic components which cannot be tailored according to the individual patient's sensitization profile. Improvement of safety and specificity of allergy vaccines has therefore been a long sought goal. The vaccination strategy of the present invention allows to generate safe, hypoallergenic allergy vaccines whenever the sequence, three-dimensional structure and/or IgE epitopes of an allergen molecule is available.

Birch pollen allergic patients IgE antibodies primarily recognize conformational Bet v 1 IgE epitopes. Surprisingly, it has been found by the inventors that hypoallergenic peptides can also be synthesized for allergens containing continuous (i.e. sequential, linear) IgE epitopes. The inventors succeeded in producing a set of hypoallergenic peptides for the major timothy grass pollen allergen, Phl p 1, which contains continuous epitopes.

Unexpectedly, peptide immunization of mice and rabbits with the peptides used in the present invention resulted in the production of IgG antibodies specific for the complete Bet v 1 wild type allergy although the peptides were rather short in length (25 to 32 amino acids) and despite the fact that certain of the peptides (P1-P3) lacked Bet v 1 specific T cell epitopes.

It was also found that peptide-induced IgG antibodies crossreacted with Bet v 1 related allergens from alder, hazel and hornbeam pollen, indicating that peptide immunotherapy may also protect against allergy to allergen sources containing a related allergen.

The peptide immunotherapy approach of the present invention is different from previously made attempts to use T cell epitope containing peptides for a modulation of allergen specific T cell responses. While administration of free, soluble T cell epitope containing peptides either aims at inducing tolerance or at switching towards Th1-responses, the inventors used adjuvant-bound, surface-exposed peptides for the focusing of blocking IgG antibodies to solvent-exposed allergen domains which can be principle targets for IgE antibodies. Since preferably adjuvant-bound peptides are used for the induction of blocking antibodies, it is unlikely that injection of peptides even when they contain T cell epitopes will cause T cell-mediated systemic reaction as has been reported for the major cat allergen, Fel d 1.

Hypoallergenic surface-exposed allergen peptides can be produced in a well controlled manner and represent therapeutic reagents which can be easily purified and standardized. Such peptides can be administered in high doses with low risk of inducing anaphylactic side effects, particularly when they are bound to adjuvants. Administration of high peptide doses is expected to induce a vigorous production of IgG antibodies which is accompanied by a Th1 immune response. The approach of selecting surface-exposed peptides according to the three-dimensional structure of important crossreactive allergens is of general applicability and allows a rational design of safe peptide-based vaccines for many other forms of type I allergy.

Description of the Tables and Figures

Table 1 summarizes the characteristics of non-allergenic Bet v 1-derived synthetic peptides. Position, sequence, length, molecular weight, isoelectric point, residual fold, presence of T cell epitopes and AGADIR prediction of six Bet v 1-derived peptides are displayed. Epitopes 1-6 are SEQ ID NOs: 1-6, respectively Table 2 shows the serological characterization of 60 birch pollen allergic patients and a non-allergic control individual (NHS). Sex, age, total serum IgE levels (kU/L), birch pollen extract-specific IgE levels (kUA/L) are displayed. IgE antibodies specific for rBet v 1 and the Bet v 1-derived peptides were measured by ELISA and OD (optical densities) are shown. Dashes indicate reactivities below the cut-off level (OD=0.050).

Table 3 summarizes immediate type skin reactions to complete rBet v 1 and Bet v 1-derived peptides. Five birch pollen allergic patients (#1-5) and an allergic individual without birch pollen allergy (#6) were tested. The mean wheal diameters (mm) are displayed for different concentrations of rBet v 1, for birch pollen extract, histamine, the individual peptides and a mixture of the six peptides.

Table 4. IgG reactivity of anti-peptide antisera with complete rBet v 1 wildtype. The upper panel shows the mean IgG reactivities (OD values) to rBet v 1 in 4 serum samples (bleeding 1: preimmune serum; bleedings 2-4: serum samples obtained in monthly intervals) of mice which were immunized with KLH-coupled peptides (P1-KLH to P6-KLH). In the lower panel, IgG reactivities to rBet v 1 are shown for 3 serum samples (bleeding 1: preimmune serum; bleedings 2-3: serum samples collected in monthly intervals) obtained from 6 rabbits of which each was immunized with one of the KLH-conjugated peptides.

Table 5. Crossreactivity of anti-Bet v 1 peptide antisera with natural allergens from birch, alder, hazel and hornbeam. IgG reactivities of peptide antisera (anti-P1 to anti-P6) to pollen extracts from birch, alder, hazel and hornbeam (mean OD values+/-SEM) are displayed for 6 groups of mice which were immunized with Bet v 1 peptides (P1-P6).

Table 6. Rabbit anti-Bet v 1 peptide antisera inhibit serum IgE binding of birch pollen allergic patients to rBet v 1. The percentage inhibition of IgE binding to complete rBet v 1 obtained with the individual anti-peptide antisera (anti-P1 to anti-P6) and a mixture of the anti-peptide antisera (anti-P1 to anti-P6) are displayed for sera from 60 birch pollen allergic patients. The bottom line summarizes the mean percentages of inhibition obtained for all serum samples.

FIG. 1 shows 1H 1D-spectra of the amide regions of the six peptides. The spectra were recorded at 20° C. on a 600 MHz spectrometer.

Figure 2:
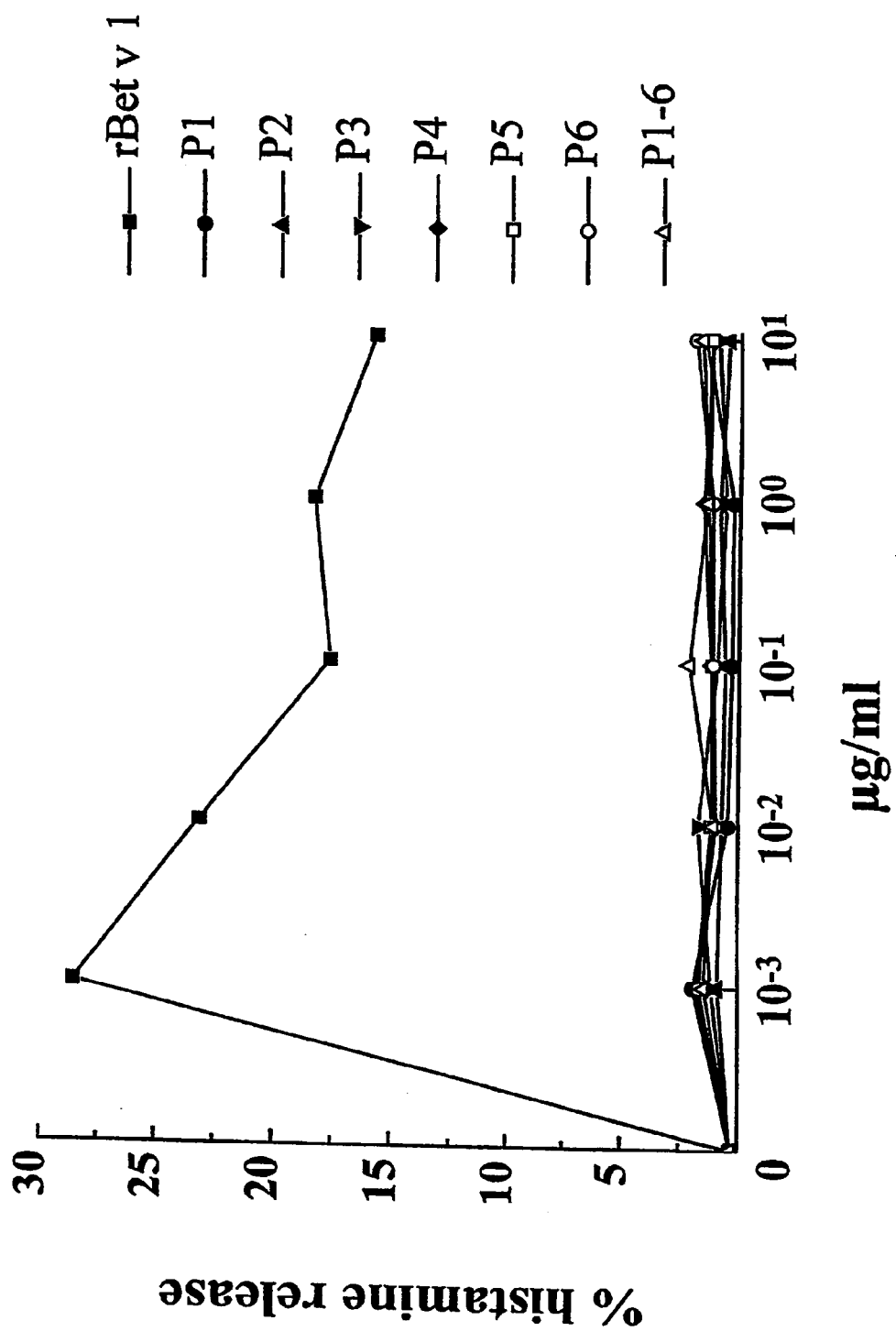

FIG. 2 shows induction of histamine release from basophils of a birch pollen allergic patient. Granulocytes of a birch pollen allergic patient were incubated with various concentrations (x-axis) of rBet v 1 wildtype, Bet v 1 derived peptides (P1, P2, P3, P4, P5, P6) and an equimolar mix of the 6 peptides (P1-P6). The percentage of histamine released into the cell-free culture supernatant is displayed on the y-axis.

Figure 3:
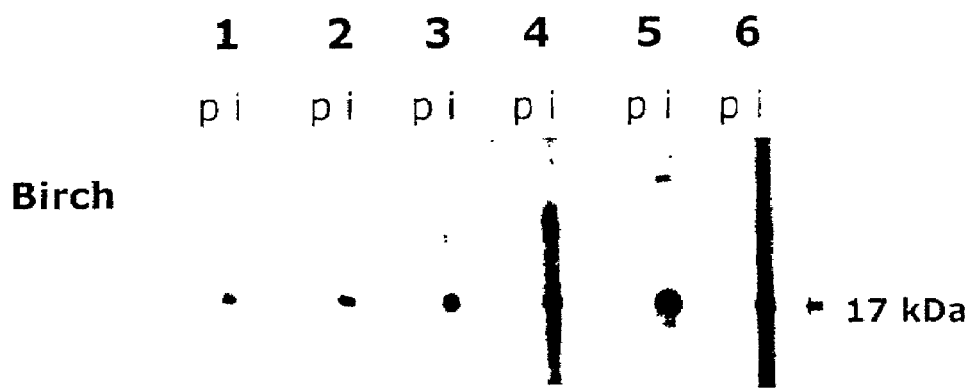

FIG. 3 shows the reactivity of peptide antisera with nitrocellulose-blotted natural Bet v 1. Nitrocellulose-blotted birch pollen extract was incubated with sera from six peptide-immunized mice (lanes i; panels 1-6: peptides 1-6). Lanes p show the corresponding preimmune sera. The position of nBet v 1 (17 kDa) is indicated.

The following examples further illustrate the invention.

EXAMPLE 1

Characteristics of Six Synthetic Peptides Spanning the Surface of the Bet v 1 Allergen Six Bet v 1-derived peptides of a length between 25 (P1: 2809.3 Dalton) to 32 (P5: 3556.1 Dalton) amino acids spanning solvent-exposed areas of the Bet v 1 molecule were selected according to the three-dimensional structure of Bet v 1 determined by x-ray crystallography and NMR (Gajhede, M. et al. (1996 X-ray and NMR structure of Bet v 1, the origin of birch pollen allergy. *Nat. Struct. Biol.* 3, 1040-1045).

The isoelectric points calculated for the 6 peptides ranges from 4.70 (P6) to 8.63 (P2) (Table 1). Three of the peptides (P4, P5, P6) comprise sequence motifs which were found to stimulate Bet v 1-specific human T cells whereas the other three peptides (P1, P2, P3) do not contain Bet v 1-specific T cell epitopes (Table 1).

TABLE 1

Characteristics of non-allergenic Bet v 1-derived synthetic peptides

| | Position aa | Sequence | No. of aa7 | Molecular Weight | Isoelectric point (pI) | Fold (NMR) | T cell epitope | Agadir % |
|---|---|---|---|---|---|---|---|---|
| SEQ ID NO:1 Peptide 1 | 1-24 | MGVFNYETETTSVIPAARLFKAFIC | 25 | 2809.3 | 6.28 | – | – | 0.86 |
| SEQ ID NO:2 Peptide 2 | 30-59 | LFPKVAPQAISSVENIEGNGGPGTIKKISFC | 31 | 3202.7 | 8.63 | – | – | 0.56 |
| SEQ ID NO:3 Peptide 3 | 50-79 | CGPGTIKKISFPEGFPFKYVKDRVDEVDHTN | 31 | 3525 | 7.00 | – | – | 0.5 |
| SEQ ID NO:4 Peptide 4 | 110-139 | DGGSILKISNKYHTKGDHEVKAEQVKASKEC | 31 | 3400.8 | 8.44 | – | + | 0.85 |
| SEQ ID NO:5 Peptide 5 | 130-160 | CKAEQVKASKEMGETLLRAVESYLLAHSDAYN | 32 | 3556.1 | 5.49 | +/− | + | 12.09 |
| SEQ ID NO:6 Peptide 6 | 75-104 | CVDHTNFKYNYSVIEGGPIGDTLEKISNEIK | 31 | 3484.9 | 4.70 | – | + | 1 | a) Peptide Synthesis

Peptides were synthesized using Fmoc (9-fluorenylmethoxycarbonyl)-strategy with HBTU (2-(1H-Benzotriazol-1-yl) 1,1,3,3 tetramethyluronium hexafluorophosphat)-activation (0.1 mmol small-scale cycles) on the Applied Biosystems peptide synthesizer Model 433A (Foster City, Calif.). Preloaded PEG-PS (polyethyleneglycol polystyrene) resins (0.15-0.2 mmol/g loading) (Per Septive Biosystems, Warrington, UK) were used as solid phase to build up the peptides. Chemicals were purchased from Applied Biosystems. Coupling of amino acids was confirmed by conductivity monitoring in a feedback control system. One cysteine residue was added to each peptide to facilitate coupling of the peptides to carriers. Peptides were cleaved from the resins with a mixture of: 250 µl dest. water, 250 µl Triisopropylsilan (Fluka, Buchs, Switzerland), 9.5 ml TFA for 2h and precipitated in tert-Butylmethylether (Fluka, Buchs, Switzerland). The identity of the peptides was checked by mass-spectrometry and they were purified to >90% purity by preparative HPLC (PiChem, Graz, Austria).

b) Secondary Structure Analysis

The six Bet v 1-derived peptides resemble almost all primary structure elements of the Bet v 1 allergen but according to AGADIR prediction and NMR analysis lack secondary structure. The AGADIR program is based on the helix-to-coil transition theory and estimates the propensity of a sequence to adopt an alpha-helical conformation irrespective of other secondary structures (Munoz, V. & Serrano, L. (1994) Elucidating the folding problem of helical peptides using empirical parameters. *Nat. Struct. Biol.* 1, 399-409). It has been shown to correctly estimate the helical behavior of a database of peptides as compared to CD (circular dichroism) and NMR data. Because it calculates the helical tendency for each amino acid in a given sequence, AGADIR may predict both the average helical population of a peptide and the propensity to populate the helical conformation for each residue. Results from these calculations are reported in Table 1. Of the peptides, only P5 shows an appreciable tendency to form a helical conformation.

c) NMR Analysis

NMR was then used to check for residual secondary or tertiary structure. Compared to other spectroscopical approaches, this technique has the advantage that it provides positional information along the sequence.

Peptides were examined for tertiary and/or secondary structure by one and two-dimensional nuclear magnetic resonance (NMR) on a UNITY VARIAN 600 MHz spectrometer equipped with z-shielded gradient coils using 0.8-1.0 mM samples in 90% $H_2O$/10% $D_2O$, 20 mM potassium phosphate buffer pH 7.0, at 20° C. Water suppression was achieved with WATERGATE. Mixing times used were 70 ms and 150 or 200 ms for TOCSY and NOESY experiments, respectively.

The appearance of the 1D experiments clearly shows absence of tertiary structure in all of the six peptides: all the resonances have poor spectral dispersion as expected for a mixture of amino acids or peptides without tertiary fold (FIG. 1). The absence of ring current shifted peaks in the region of the spectra below 0.5 ppm typical of well folded proteins is also a feature common to the spectra of the Bet v 1 peptides (data not shown). However, the spectrum of P5 contains unusually broad resonances suggesting aggregation of this peptide. This peptide (P5), that in the Bet v 1 structure spans the whole C-terminal helix probably tends to form helical structures that aggregate in water solution.

EXAMPLE 2

Surface Exposed Bet v 1-Derived Peptides Lack IgE Binding Capacity and Allergenic Activity a) IgE Binding Capacity The IgE binding capacity of the six Bet v 1-derived peptides was compared with that of the complete rBet v 1 wildtype allergen using sera from 60 birch pollen allergic patients (Table 2).

Characterization of Allergic Patients and Patients Sera

Birch pollen allergic patients suffering from allergic rhinoconjunctivitis and/or asthma to birch pollen and related allergens were selected according to case history indicative for seasonal birch pollinosis and characterized by skin prick testing with birch pollen extract and serological CAP RAST (Pharmacia Diagnostics, Uppsala, Sweden) testing. Total IgE levels in the sera were determined by CAP RIST measurements (Pharmacia). IgE antibodies specific for rBet v 1 were determined by ELISA (Niederberger et al. (1998) IgE antibodies to recombinant pollen allergens (Phl p 1, Phl p 2, Phl p 5, and Bet v 2) account for a high percentage of grass pollen-specific IgE. *J. Allergy Clin. Immunol.* 101, 258-264). Sera from 60 birch pollen allergic patients and a non-atopic individual were used for IgE competition studies. The birch pollen allergic patients group consisted of 25 males and 35 females with a mean age of 37 years (ranging from 19-60 years) (Table 2).

Result

Total IgE levels and IgE levels specific for birch pollen extract ranged from 24-2000 kU/L (mean: 300) and 3-100 kUA/L (mean: 47), respectively. All patients contained rBet v1-specific IgE antibodies ranging between 0.081-2.530 OD units (mean: 1.416 OD units) (Table 2). When tested for IgE reactivity to ELISA plate bound peptides (P1-P6) no serum showed significant IgE reactivity above the cut off level determined with serum from a non-atopic person (NHS) (Table 2).

TABLE 2

Serological characterization of birch pollen allergic patients

| Patient | sex | age | total IgE (kU/L) | IgE birch (kUA/L) | rBet v 1 | P1 | P2 | P3 | P4 | P5 | P6 |
|---|---|---|---|---|---|---|---|---|---|---|---|
| 1 | w | 27 | 204 | 27.2 | 0.829 | — | — | — | — | — | — |
| 2 | w | 54 | 617 | 69.9 | 1.380 | — | — | — | — | — | — |
| 3 | m | 55 | 592 | 100.0 | 2.144 | — | — | — | — | — | — |
| 4 | w | 35 | 109 | 34.9 | 0.701 | — | — | — | — | — | — |
| 5 | w | 35 | 41.5 | 21.1 | 0.344 | — | — | — | — | — | — |
| 6 | m | 27 | 1642 | 77.0 | 2.300 | — | — | — | — | — | — |
| 7 | m | 24 | 2000 | 96.9 | 2.245 | — | — | — | — | — | — |
| 8 | m | 60 | 235 | 49.6 | 0.950 | — | — | — | — | — | — |
| 9 | w | 56 | 35.4 | 8.7 | 0.196 | — | — | — | — | — | — |
| 10 | w | 32 | 46.6 | 5.8 | 0.097 | — | — | — | — | — | — |
| 11 | w | 23 | 121 | 23.4 | 0.428 | — | — | — | — | — | — |
| 12 | m | 24 | 122 | 17.6 | 0.271 | — | — | — | — | — | — |
| 13 | w | 21 | 238 | 55.4 | 0.281 | — | — | — | — | — | — |
| 14 | w | 26 | 124 | 41.7 | 0.704 | — | — | — | — | — | — |
| 15 | m | 38 | 95.3 | 41.6 | 0.606 | — | — | — | — | — | — |
| 16 | m | 37 | 147 | 11.7 | 0.215 | — | — | — | — | — | — |
| 17 | m | 20 | 206 | 5.0 | 0.622 | — | — | — | — | — | — |
| 18 | w | 43 | 135 | 50.9 | 0.663 | — | — | — | — | — | — |

TABLE 2-continued

Serological characterization of birch pollen allergic patients

| Patient | sex | age | total IgE (kU/L) | IgE birch (kUA/L) | rBet v 1 | P1 | P2 | P3 | P4 | P5 | P6 |
|---|---|---|---|---|---|---|---|---|---|---|---|
| 19 | w | 39 | 267 | 79.8 | 1.166 | — | — | — | — | — | — |
| 20 | w | 50 | 28.1 | 13.2 | 0.249 | — | — | — | — | — | — |
| 21 | m | 60 | 36.9 | 26.1 | 0.461 | — | — | — | — | — | — |
| 22 | w | 44 | 59.7 | 23.5 | 0.258 | — | — | — | — | — | — |
| 23 | m | 34 | 153 | 30.8 | 1.555 | — | — | — | — | — | — |
| 24 | w | 35 | 84.6 | 16.4 | 0.237 | — | — | — | — | — | — |
| 25 | w | 55 | 152 | 39.2 | 0.5 | — | — | — | — | — | — |
| 26 | m | 53 | 31.5 | 8.5 | 0.191 | — | — | — | — | — | — |
| 27 | m | 41 | 89.9 | 33.0 | 0.535 | — | — | — | — | — | — |
| 28 | w | 37 | 61.6 | 39.8 | 0.492 | — | — | — | — | — | — |
| 29 | w | 50 | 65.2 | 10.0 | 0.154 | — | — | — | — | — | — |
| 30 | m | 41 | 260 | 87.5 | 0.081 | — | — | — | — | — | — |
| 31 | m | 52 | 450 | 73.5 | 1.168 | — | — | — | — | — | — |
| 32 | w | 34 | 70.2 | 13.7 | 0.195 | — | — | — | — | — | — |
| 33 | w | 30 | 293 | 9.9 | 0.106 | — | — | — | — | — | — |
| 34 | m | 24 | 309 | 32.0 | 0.377 | — | — | — | — | — | — |
| 35 | w | 39 | 273 | 84.6 | 0.601 | — | — | — | — | — | — |
| 36 | m | 39 | 257 | 31.1 | 0.306 | — | — | — | — | — | — |
| 37 | m | 49 | 208 | 68.9 | 0.227 | — | — | — | — | — | — |
| 38 | w | 46 | 208 | 79.7 | 1.571 | — | — | — | — | — | — |
| 39 | m | 53 | 125 | 51.3 | 0.620 | — | — | — | — | — | — |
| 40 | w | 23 | 121 | 5.7 | 0.084 | — | — | — | — | — | — |
| 41 | w | 29 | 490 | 100.0 | 1.193 | — | — | — | — | — | — |
| 42 | w | 51 | 370 | 100.0 | 1.119 | — | — | — | — | — | — |
| 43 | m | 19 | 1234 | 100.0 | 0.363 | — | — | — | — | — | — |
| 44 | w | 23 | 589 | 100.0 | 2.386 | — | — | — | — | — | — |
| 45 | w | 25 | 278 | 54.5 | 0.289 | — | — | — | — | — | — |
| 46 | w | 35 | 184 | 47.5 | 0.892 | — | — | — | — | — | — |
| 47 | m | 23 | 207 | 30.2 | 0.381 | — | — | — | — | — | — |
| 48 | w | 33 | 200 | 47.5 | 1.422 | — | — | — | — | — | — |
| 49 | w | 24 | 297 | 23.4 | 0.379 | — | — | — | — | — | — |
| 50 | w | 26 | 24 | 11.5 | 0.220 | — | — | — | — | — | — |
| 51 | m | 29 | 543 | 100.0 | 0.307 | — | — | — | — | — | — |
| 52 | w | 48 | 178 | 17.5 | 0.208 | — | — | — | — | — | — |
| 53 | w | 33 | 152 | 100.0 | 1.256 | — | — | — | — | — | — |
| 54 | w | 36 | 187 | 64.7 | 1.310 | — | — | — | — | — | — |
| 55 | m | 26 | 2000 | 100.0 | 2.489 | — | — | — | — | — | — |
| 56 | m | 35 | 1733 | 100.0 | 2.530 | — | — | — | — | — | — |
| 57 | w | 28 | 270 | 62.5 | 0.741 | — | — | — | — | — | — |
| 58 | m | 41 | 80 | 3.0 | 0.072 | — | — | — | — | — | — |
| 59 | m | 49 | 41.9 | 12.9 | 0.168 | — | — | — | — | — | — |
| 60 | w | 35 | 84.6 | 16.4 | 0.237 | — | — | — | — | — | — |
| NHS | W | 40 | 5 | <0.35 | 0.048 | — | — | — | — | — | — | b) Histamine Release

Next the Bet v 1-derived peptides were compared with complete rBet v 1 for their capacity to induce histamine release from basophilic granulocytes of 3 birch pollen allergic individuals.

Basophil Histamine-release Assay

Granulocytes were isolated from heparinized blood samples of 3 birch pollen allergic individuals by dextran sedimentation (Valent, P. et al. (1989) Interleukin 3 activates human blood basophils via high-affinity binding sites. *Proc. Natl. Sci. USA* 86, 5542-5547). Cells were incubated with increasing concentrations ($10^{-3}$-10 μg/ml) of each peptide, an equimolar mix of the 6 peptides, and, for control purposes, with complete rBet v 1. Histamine released in the cell-free culture supernatant was measured by radioimmunoassay (Immunotech, Marseille, France). Total histamine was determined after freezing and thawing of cells. Results are displayed as mean values of triplicate determinations.

Result

As exemplified in FIG. 2 it was found that none of the peptides induced release of histamine up to concentrations of 10 μg/ml whereas complete rBet v 1 wildtype induced a dose-dependent release of histamine with a maximum release already at a concentration of 1 ng/ml.

c) Allergenic Activity in vivo

In vivo testing in birch pollen allergic patients confirmed the lack of allergenic activity of the Bet v 1-derived peptides.

Skin Prick Testing of Allergic Patients

The in vivo allergenic activity of the peptides was studied by skin prick testing (SPT) in 5 birch pollen allergic patients and a non-atopic grass pollen allergic patient without birch pollen allergy. SPTs were performed on the individuals forearms as described (Vrtala, S. et al. (1997) *J. Clin Invest.* 99, 1673-168; Dreborg S: (1989) *J. Am. Acad. DerMatol.* 21, 820-821). Twenty microliter aliquots containing 6 concentrations of complete rBet v 1 (0.78 μg/ml, 1.56 μg/ml, 3.12 μg/ml, 6.25 μg/ml, 12.5 μg/ml, 25 μg/ml), 100 μg/ml of each peptide and an equimolar peptide mix were applied. In addition standardized skin prick solutions (birch pollen extract and histamine) (Allergopharma, Reinbek, Germany) were tested. Reactions were recorded 20 minutes after SPT by photography and by transferring the ballpoint pen-surrounded wheal area with a scotch tape to paper. The mean wheal diameter (Dm) was calculated by measuring the maximal longitudinal and transversal diameter and dividing their sum by 2.

Result

Skin prick tests were performed in 5 birch pollen allergic patients and an allergic individual without birch pollen allergy with rBet v 1 and Bet v 1-derived peptides (Table 3). None of the Bet v 1-derived peptides induced any immediate skin reaction when applied at a concentration of 100 µg/ml or as peptide mixture containing 100 µg/ml of each peptide (Table 3). Complete rBet v 1 wildtype already induced immediate type skin reactions in three patients (Table 3: #1-3) at a concentration of <0.78 µg/ml. A concentration of 3.12 µg/ml was sufficient to induce wheal reactions in all five birch pollen allergic patients (Table 3). All birch pollen allergic patients displayed immediate skin reactions to birch pollen extract. The grass pollen allergic patient without birch pollen allergy (Table 3: #6) showed no reactions to birch pollen extract, rBet v 1 and Bet v 1-derived peptides (Table 3) but exhibited a wheal reaction after prick testing with timothy grass pollen extract (5.5 mm mean diameter) (data not shown). All individuals reacted after testing with histamine, used as a positive control (Table 3). Since local and even systemic late phase reactions to allergens and in particular to allergen-derived non-allergenic peptides have been reported we checked the application sites 24-48 hours after skin prick testing but found no evidence for peptide-induced late phase reactions in any of the tested individuals (data not shown).

University of Vienna, according to the local guidelines for animal care. Groups of 5 animals were immunized with conjugated and unconjugated peptides adsorbed to AluGel (Serva, Heidelberg, Germany). Each mouse received four 100 µl-injections (20 µg peptide or peptide-KLH conjugate adsorbed to 15 µg of $Al(OH)_3$) subcutaneously in the neck in four week intervals. Shortly before each injection and four weeks after the last immunization, mice were bled from the tail veins. Sera were stored at −20° C. until analysis.

In parallel six rabbits were immunized with one of the peptide-KLH conjugates (200 µg/injection) using Freunds complete and incomplete adjuvants (Charles River, KiBlegg, Germany). Serum samples were obtained in four week intervals.

Crossreactivity of Anti-Peptide Antisera

Reactivity of peptide-induced IgG antibodies to rBet v 1, natural Bet v 1 and Bet v 1-related pollen and plant food allergens was studied by ELISA and immunoblotting. For ELISA detection, plates (Nunc Maxisorp, Roskilde, Denmark) were coated with pollen allergen extracts (100 µg/ml: *Betula verrucosa, Alnus glutinosa, Corylus avellana* and *Carpinus betulus*) or purified allergens (5 µg/ml: rBet v 1). ELISA plates were washed and blocked as described (Niederberger, V. et al. (1998). *J. Allergy Clin. Immunol.* 101, 258-264) and subsequently incubated with mouse anti-peptide antisera diluted 1:500. Bound mouse $IgG_1$ antibodies were detected with a monoclonal rat anti mouse $IgG_1$ antibody (Pharmingen, San Diego, Calif.) diluted 1:1000 followed by a 1:2000 diluted HRP-coupled sheep anti-rat Ig

TABLE 3

Induction of immediate skin reaction with rBet v 1 and Bet v 1-derived peptides mean wheal diameter

| Individual | rBet v 1 µg/ml | | | | | | | | birch | histamine | 100 µg/ml | | | | | | |
|---|---|---|---|---|---|---|---|---|---|---|---|---|---|---|---|---|---|
| | 0.19 | 0.39 | 0.78 | 1.56 | 3.12 | 6.25 | 12.5 | 25 | | | P1 | P2 | P3 | P4 | P5 | P6 | P1–P6 mix |
| 1 | 0 | 2.5 | 4 | 4.5 | 5 | 6 | 13 | n.d. | 5.5 | 5 | 0 | 0 | 0 | 0 | 0 | 0 | 0 |
| 2 | 0 | 2 | 3.5 | 5 | 5.5 | 7 | 7.5 | 8 | 7.5 | 6 | 0 | 0 | 0 | 0 | 0 | 0 | 0 |
| 3 | n.d. | n.d. | 2 | 3 | 4 | 6 | 6.5 | 8 | 8 | 7 | 0 | 0 | 0 | 0 | 0 | 0 | 0 |
| 4 | n.d. | n.d. | 0 | 0 | 2 | 3 | 4 | 4.5 | 8 | 5 | 0 | 0 | 0 | 0 | 0 | 0 | 0 |
| 5 | n.d. | n.d. | 0 | 2 | 2.5 | 4 | 11 | 5 | 9 | 5.5 | 0 | 0 | 0 | 0 | 0 | 0 | 0 |
| 6 | n.d. | n.d. | 0 | 0 | 0 | 0 | 0 | 0 | 0 | 4 | 0 | 0 | 0 | 0 | 0 | 0 | 0 |

EXAMPLE 3

Immunization with Bet v 1-Derived Peptides Induces IgG Antibodies Reactive with Complete Bet v 1 and Bet v 1-Related Plant Allergens a) Induction of IgG Antibodies In order to test whether immunization with Bet v 1-derived peptides will induce IgG antibodies that react with the complete Bet v 1 molecule and Bet v 1-related allergens mice and rabbits were immunized with the KLH-conjugated peptides using different adjuvants (Aluminiumhydroxide, Freund's adjuvant).

Immunization of Mice and Rabbits

HPLC-purified peptides were coupled to KLH (keyhole limpet hemocyanin, MW $4.5 \times 10^3$-$1.3 \times 10^7$, Pierce, Rockford, Ill.) according to the manufacturers advice and purified using a Conjugation Kit (Sigma, St. Louis). KLH-conjugated peptides were used to immunize mice and rabbits using $Al(OH)_3$ and CFA as adjuvant, respectively. Six week old female BALB/c mice were purchased from Charles River (KiBlegg, Germany). Animals were maintained in the animal care unit of the Department of Pathophysiology, antiserum (Amersham Pharmacia Biotech, Uppsala, Sweden). Results represent means of duplicate determination with an error of <5% and are displayed as means +/− SEM for the group of 5 mice. ELISAs with rabbit anti-peptide antisera were performed as described for the mouse sera with the exception that rabbit sera were diluted 1:1000 and bound rabbit antibodies were detected with a HRP-coupled goat anti-rabbit Ig antiserum (Jackson Immunresearch, Pennyslvania).

Immunoblotting experiments were performed with nitrocellulose-blotted allergens. Pollen extracts and plant food extracts were separated by 12.5% preparative SDS-PAGE (12 µg/cm gel) and blotted onto nitrocellulose membranes (Schleicher & Schuell, Dassel, Germany). Nitrocellulose membranes were exposed to 1:1000 diluted rabbit sera (preimmune, immune sera) and in certain experiments, with sera from mice which were immunized with unconjugated $Al(OH)_3$-adsorbed peptides. Bound rabbit antibodies were detected with a 1:2000 diluted $^{125}$I-labeled donkey anti-rabbit IgG antiserum (Amersham Pharmacia Biotech). Bound mouse antibodies were detected with a 1:2500 diluted rabbit anti-mouse IgG antiserum (Jackson Immunresearch) followed by 1:2000 diluted $^{125}$I-labeled donkey anti-rabbit IgG antiserum (Amersham).

Result

Table 4A shows the development of IgG anti-rBet v 1 antibody responses in groups of mice which were immunized with Al(OH)$_3$-adsorbed, KLH-conjugated peptides. All 6 peptides induced IgG anti-rBet v 1 antibody responses which could be detected 4-8 weeks after the first immunization (Table 4A: bleeding 2-3). Peptide-induced IgG anti-rBet v 1 responses constantly increased during the immunization. Using unconjugated peptides, anti-rBet v 1 IgG antibody responses could be induced, albeit of a lower magnitude (data not shown).

Similar results were obtained after immunization of rabbits with KLH-conjugated peptides which were administered s.c. together with Freund's adjuvant (Table 4B). All 6 peptides induced IgG anti-rBet v 1 antibody responses which increased during the course of immunization. Peptide-induced mouse IgG antibodies reacted also with nitrocellulose-blotted pollen-derived natural Bet v 1 whereas no signals were obtained with the corresponding preimmune sera (FIG. 3).

(Välinge, Sweden). Aqueous pollen extracts were prepared and checked for quantity and quality of proteins by SDS-PAGE and Coomassie blue staining (Vrtala, S. et al. (1993) *Int. Arch. Allergy Immunol.* 102, 160-169). Purified recombinant Bet v 1 was purchased from BIOMAY (Linz, Austria).

Result

Table 5 shows that almost all anti-Bet v 1 peptide antisera contained IgG antibodies to natural Bet v 1 and Bet v 1-related Fagales pollen allergens. Only anti-peptide 4 antibodies showed weak reactivity with the major hazel pollen allergen, Cor a 1, and anti-peptide 6 antibodies reacted weakly with the major alder and hazel pollen allergen, Aln g 1 and Cor a 1, respectively.

TABLE 4

| bleeding | P1-KLH | P2-KLH | P3-KLH | P4-KLH | P5-KLH | P6-KLH |
|---|---|---|---|---|---|---|
| IgG reactivity of mouse anti-peptide antisera with rBet v 1 | | | | | | |
| 1 | 0.040 | 0.040 | 0.040 | 0.040 | 0.042 | 0.040 |
| 2 | 0.057 | 0.335 | 1.150 | 0.433 | 0.872 | 0.152 |
| 3 | 0.289 | 0.858 | 1.380 | 1.177 | 1.621 | 0.705 |
| 4 | 0.394 | 1.182 | 2.025 | 1.965 | 2.274 | 1.337 |
| IgG reactivity of rabbit anti-peptide antisera with rBet v 1 | | | | | | |
| 1 | 0.170 | 0.044 | 0.046 | 0.044 | 0.033 | 0.051 |
| 2 | 0.642 | 0.702 | 0.511 | 0.501 | 0.917 | 0.997 |
| 3 | 0.751 | 1.201 | 0.961 | 0.926 | 1.503 | 0.751 |

TABLE 5

Crossreactivity of anti-Bet v 1 peptide antisera with natural allergens from birch, alder, hazel and hornbeam

| | anti-P1 | anti-P2 | anti-P3 | anti-P4 | anti-P5 | anti-P6 |
|---|---|---|---|---|---|---|
| birch | 0.301 ± 0.198 | 0.841 ± 0.465 | 1.330 ± 0.172 | 1.135 ± 0.312 | 1.945 ± 0.329 | 0.898 ± 0.434 |
| alder | 0.307 ± 0.232 | 0.875 ± 0.453 | 0.619 ± 0.314 | 0.330 ± 0.265 | 1.613 ± 0.477 | 0.084 ± 0.032 |
| hazel | 0.217 ± 0.200 | 0.350 ± 0.297 | 0.071 ± 0.018 | 0.073 ± 0.022 | 1.239 ± 0.397 | 0.060 ± 0.007 |
| hornbeam | 0.253 ± 0.209 | 0.559 ± 0.373 | 0.183 ± 0.117 | 0.233 ± 0.145 | 1.369 ± 0.234 | 0.449 ± 0.490 | b) Reactivity of Induced IgG Antibodies with Bet v 1-Related Plant Allergens

Next it was investigated whether anti-Bet v 1 peptide antisera crossreact with Bet v 1-related allergens present in pollens of alder, hazel and hornbeam.

Allergen Extracts

Pollen from trees of the order Fagales (birch: *Betula verrucosa*; alder: *Alnus glutinosa*; hazel: *Corylus avellana*; hornbeam: *Carpinus betulus*) were purchased from Allergon

EXAMPLE 4

Anti-Peptide Antisera Inhibit the Binding of Birch Pollen Allergic Patients Ige to Complete Bet v 1

The capacity of anti-Bet v 1 peptide antibodies to inhibit the binding of allergic patients IgE to complete rBet v 1 was studied by ELISA competition using sera from 60 birch pollen allergic patients' (Tables 2 and 6).

Elisa Detection of Peptide and rBet v 1-Specific Ige Antibodies:

Inhibition of allergic patients IgE binding to rBet v 1 by peptide-induced IgG. ELISA plates (Nunc Maxisorp, Roskilde, Denmark) were coated with Bet v 1-derived peptides (5 µg/ml) or rBet v 1 as control (5 µg/ml), washed and blocked as described in Example 3. Subsequently, plates were incubated with 1:3 diluted sera from 60 birch pollen allergic patients and from a non-atopic individual overnight at 4° C. Bound IgE antibodies were detected with a 1:1000 diluted alkaline-phosphatase-coupled mouse monoclonal anti-human IgE antibody (Pharmingen, San Diego, Calif.).

The ability of peptide-induced rabbit Ig to inhibit the binding of allergic patients' IgE to complete rBet v 1 was investigated by ELISA competition assay as described (Denepoux et al. (2000) *FEBS Lett.* 465, 39-46). ELISA plates were coated with rBet v 1 (1 µg/ml) and preincubated either with a 1:250 dilution of each of the anti-peptide antisera (anti-P1-anti-P6), a mixture containing equal volumes of the anti-peptide antisera and, for control purposes, with the corresponding preimmune sera and a mixture of the preimmune sera as described. After washing plates were incubated with 1:3 diluted sera from 60 birch pollen allergic patients and bound IgE antibodies were detected with the alkaline phosphatase-coupled mouse monoclonal anti-human IgE antibody (Pharmingen). The percentage inhibition of IgE binding achieved by preincubation with the anti-peptide antisera was calculated as follows: % inhibition of IgE binding=$100-OD_I/OD_P \times 100$. $OD_I$ and $OD_P$ represent the extinctions after preincubation with the rabbits immune and preimmune serum, respectively.

Result:

All birch pollen allergic patients tested exhibited immediate type skin reactions to birch pollen extract. For all but three sera (serum #9, 10, 38), preincubation with peptide-induced rabbit IgG inhibited considerably the binding of human IgE to Bet v 1. The strongest inhibition of igE binding was observed after preincubation with anti-P2 (68% average inhibition), anti-P6 (60% average inhibition), anti-P3 (53.6% average inhibition) and anti-P5 (41.6% average inhibition). Anti-P4 antibodies exhibited a lower capacity to inhibit serum IgE binding to Bet v 1 (average inhibition 28.5%) and anti-P1 antibodies raised against the N-terminus of Bet v 1 weakly inhibited IgE binding to Bet v 1 (average inhibition 11.4%). Interestingly, a mixture of anti-P1 to anti-P6 antibodies did not exhibit a stronger inhibition of IgE binding (average inhibition 56.9%) than antibodies induced against single peptides (e.g., anti-P2-, anti-P6 antibodies) (Table 6). No association between the levels of rBet v 1-specific IgE in the sera and the degree of inhibition of IgE binding by the anti-peptide antisera was observed.

TABLE 6

Rabbit anti-Bet v 1 peptide antisera inhibit serum IgE binding of birch pollen allergic patients to rBet v 1

| | % inhibition | | | | | | |
|---|---|---|---|---|---|---|---|
| Patient | anti-P1 | anti-P2 | anti-P3 | anti-P4 | anti-P5 | anti-P6 | anti-P1–6 |
| 1 | 16 | 82 | 76 | 59 | 72 | 80 | 86 |
| 2 | 0 | 88 | 78 | 49 | 70 | 76 | 85 |
| 3 | 16 | 92 | 86 | 50 | 76 | 85 | 92 |
| 4 | 39 | 66 | 47 | 28 | 38 | 60 | 67 |
| 5 | 0 | 75 | 44 | 60 | 31 | 62 | 48 |
| 6 | 0 | 88 | 75 | 38 | 59 | 76 | 90 |
| 7 | 20 | 92 | 80 | 40 | 68 | 86 | 93 |
| 8 | 17 | 68 | 69 | 44 | 66 | 65 | 67 |
| 9 | 13 | 0 | 0 | 0 | 0 | 0 | 0 |
| 10 | 0 | 0 | 0 | 0 | 0 | 0 | 0 |
| 11 | 34 | 70 | 55 | 0 | 13 | 56 | 62 |
| 12 | 10 | 44 | 41 | 24 | 27 | 28 | 0 |
| 13 | 18 | 54 | 62 | 31 | 33 | 53 | 0 |
| 14 | 12 | 72 | 51 | 0 | 52 | 61 | 48 |
| 15 | 0 | 51 | 6 | 18 | 14 | 51 | 6 |
| 16 | 13 | 81 | 56 | 27 | 52 | 72 | 69 |
| 17 | 13 | 87 | 75 | 48 | 46 | 80 | 86 |
| 18 | 15 | 89 | 73 | 44 | 65 | 85 | 90 |
| 19 | 46 | 82 | 35 | 0 | 51 | 61 | 92 |
| 20 | 0 | 85 | 61 | 34 | 59 | 77 | 84 |
| 21 | 14 | 69 | 54 | 13 | 44 | 56 | 53 |
| 22 | 0 | 72 | 62 | 35 | 52 | 65 | 71 |
| 23 | 17 | 86 | 74 | 51 | 69 | 81 | 87 |
| 24 | 11 | 68 | 39 | 19 | 43 | 51 | 37 |
| 25 | 15 | 83 | 73 | 48 | 67 | 77 | 78 |
| 26 | 8 | 51 | 37 | 31 | 29 | 51 | 0 |
| 27 | 0 | 79 | 65 | 33 | 60 | 78 | 84 |
| 28 | 5 | 72 | 59 | 17 | 45 | 70 | 75 |
| 29 | 0 | 66 | 44 | 21 | 38 | 41 | 33 |
| 30 | 0 | 40 | 18 | 0 | 0 | 31 | 13 |
| 31 | 6 | 79 | 80 | 25 | 66 | 46 | 82 |
| 32 | 7 | 79 | 67 | 38 | 51 | 68 | 78 |
| 33 | 0 | 22 | 21 | 4 | 20 | 21 | 0 |
| 34 | 0 | 62 | 44 | 7 | 47 | 51 | 65 |
| 35 | 0 | 72 | 57 | 16 | 45 | 64 | 61 |
| 36 | 13 | 69 | 52 | 12 | 46 | 57 | 54 |
| 37 | 2 | 22 | 23 | 7 | 12 | 14 | 0 |
| 38 | 0 | 0 | 0 | 0 | 0 | 0 | 0 |
| 39 | 0 | 89 | 66 | 0 | 50 | 80 | 87 |
| 40 | 9 | 78 | 63 | 32 | 61 | 79 | 66 |
| 41 | 16 | 90 | 80 | 64 | 49 | 87 | 91 |
| 42 | 11 | 89 | 76 | 49 | 45 | 79 | 86 |
| 43 | 25 | 80 | 69 | 28 | 3 | 81 | 74 |
| 44 | 0 | 67 | 28 | 17 | 8 | 50 | 62 |
| 45 | 23 | 82 | 73 | 37 | 76 | 76 | 80 |
| 46 | 23 | 84 | 85 | 47 | 76 | 82 | 86 |
| 47 | 5 | 73 | 64 | 18 | 32 | 60 | 42 |
| 48 | 7 | 82 | 65 | 38 | 20 | 71 | 83 |
| 49 | 2 | 74 | 68 | 38 | 56 | 63 | 48 |
| 50 | 13 | 64 | 42 | 35 | 29 | 62 | 58 |
| 51 | 20 | 47 | 42 | 15 | 0 | 28 | 27 |
| 52 | 14 | 55 | 38 | 35 | 15 | 48 | 13 |
| 53 | 7 | 87 | 69 | 52 | 34 | 80 | 85 |
| 54 | 37 | 82 | 81 | 71 | 79 | 78 | 74 |
| 55 | 16 | 82 | 52 | 29 | 39 | 72 | 85 |
| 56 | 21 | 87 | 74 | 51 | 61 | 81 | 88 |
| 57 | 30 | 75 | 60 | 45 | 55 | 66 | 65 |
| 58 | 4 | 23 | 0 | 0 | 0 | 28 | 9 |
| 59 | 7 | 62 | 43 | 17 | 41 | 59 | 13 |
| 60 | 11 | 68 | 39 | 19 | 43 | 51 | 37 |
| mean | 11.4 | 68.0 | 53.6 | 28.5 | 41.6 | 60.0 | 56.9 |

The invention claimed is:

1. A pharmaceutical composition comprising a pharmaceutically acceptable carrier or diluent and a peptide for use as immunotherapeutic agent capable of inducing IgG antibodies response to allergenic proteins without inducing IgE-mediated allergic reaction wherein the peptide:
   a) has an amino acid sequence obtained from the birch pollen allergen Bet v 1;
   b) has a length of at least 8 and no more than 50 amino acids;
   c) has at least three consecutive amino acids identical to at least three solvent-exposed amino acids of an allergenic protein which appear in close vicinity on the molecular surface of the allergenic protein;
   d) is upon administration capable of inducing IgG antibodies to the allergenic protein and
   e) does not induce an IRE-mediated allergic reaction; and
   wherein the peptide is any one of Seq. ID. Nos. 1 to 6.

* * * * *

UNITED STATES PATENT AND TRADEMARK OFFICE
CERTIFICATE OF CORRECTION

PATENT NO. : 7,244,431 B2
APPLICATION NO. : 10/026911
DATED : July 17, 2007
INVENTOR(S) : Margarete Focke et al.

It is certified that error appears in the above-identified patent and that said Letters Patent is hereby corrected as shown below:

<u>Claims,</u>
Column 20,
Line 33, "IRE-mediated" should read --"IGE-mediated--

Signed and Sealed this

Fourth Day of March, 2008

JON W. DUDAS
*Director of the United States Patent and Trademark Office*

SEQUENCE LISTING

<160> NUMBER OF SEQ ID NOS: 6

<210> SEQ ID NO 1
<211> LENGTH: 25
<212> TYPE: PRT
<213> ORGANISM: Artificial Sequence
<220> FEATURE:
<223> OTHER INFORMATION: Description of Artificial Sequence:
      solvent-exposed peptide

<400> SEQUENCE: 1

Met Gly Val Phe Asn Tyr Glu Thr Glu Thr Thr Ser Val Ile Pro Ala
 1               5                  10                  15

Ala Arg Leu Phe Lys Ala Phe Ile Cys
            20                  25

<210> SEQ ID NO 2
<211> LENGTH: 31
<212> TYPE: PRT
<213> ORGANISM: Artificial Sequence
<220> FEATURE:
<223> OTHER INFORMATION: Description of Artificial Sequence:
      solvent-exposed peptide

<400> SEQUENCE: 2

Leu Phe Pro Lys Val Ala Pro Gln Ala Ile Ser Ser Val Glu Asn Ile
 1               5                  10                  15

Glu Gly Asn Gly Gly Pro Gly Thr Ile Lys Lys Ile Ser Phe Cys
            20                  25                  30

<210> SEQ ID NO 3
<211> LENGTH: 31
<212> TYPE: PRT
<213> ORGANISM: Artificial Sequence
<220> FEATURE:
<223> OTHER INFORMATION: Description of Artificial Sequence:
      solvent-exposed peptide

<400> SEQUENCE: 3

Cys Gly Pro Gly Thr Ile Lys Lys Ile Ser Phe Pro Glu Gly Phe Pro
 1               5                  10                  15

Phe Lys Tyr Val Lys Asp Arg Val Asp Glu Val Asp His Thr Asn
            20                  25                  30

<210> SEQ ID NO 4
<211> LENGTH: 31
<212> TYPE: PRT
<213> ORGANISM: Artificial Sequence
<220> FEATURE:
<223> OTHER INFORMATION: Description of Artificial Sequence:
      solvent-exposed peptide

<400> SEQUENCE: 4

Asp Gly Gly Ser Ile Leu Lys Ile Ser Asn Lys Tyr His Thr Lys Gly
 1               5                  10                  15

Asp His Glu Val Lys Ala Glu Gln Val Lys Ala Ser Lys Glu Cys
            20                  25                  30

<210> SEQ ID NO 5
<211> LENGTH: 32
<212> TYPE: PRT
<213> ORGANISM: Artificial Sequence
<220> FEATURE:
<223> OTHER INFORMATION: Description of Artificial Sequence:

solvent-exposed peptide

<400> SEQUENCE: 5

Cys Lys Ala Glu Gln Val Lys Ala Ser Lys Glu Met Gly Glu Thr Leu
 1               5                  10                  15

Leu Arg Ala Val Glu Ser Tyr Leu Leu Ala His Ser Asp Ala Tyr Asn
                20                  25                  30

<210> SEQ ID NO 6
<211> LENGTH: 31
<212> TYPE: PRT
<213> ORGANISM: Artificial Sequence
<220> FEATURE:
<223> OTHER INFORMATION: Description of Artificial Sequence:
      solvent-exposed peptide

<400> SEQUENCE: 6

Cys Val Asp His Thr Asn Phe Lys Tyr Asn Tyr Ser Val Ile Glu Gly
 1               5                  10                  15

Gly Pro Ile Gly Asp Thr Leu Glu Lys Ile Ser Asn Glu Ile Lys
                20                  25                  30